United States Patent [19]

Hackler et al.

[11] Patent Number: 5,811,461
[45] Date of Patent: Sep. 22, 1998

[54] BENZOYLPHENYLUREA INSECTICIDES AND METHODS OF USING THEM TO CONTROL COCKROACHES, ANTS, FLEAS, AND TERMITES

[75] Inventors: Ronald E. Hackler; George W. Johnson, both of Indianapolis; John M. Owen, Greenfield, all of Ind.

[73] Assignee: Dow AgroSciences LLC, Indianapolis, Ind.

[21] Appl. No.: 962,387

[22] Filed: Oct. 31, 1997

[51] Int. Cl.⁶ .......................... A01N 47/34; C07C 275/54
[52] U.S. Cl. .......................... 514/594; 424/410; 424/416; 564/44
[58] Field of Search ............... 514/594; 564/44; 424/410, 416

[56] References Cited

U.S. PATENT DOCUMENTS

| | | | |
|---|---|---|---|
| 3,748,356 | 7/1973 | Wellinga et al. | 260/553 E |
| 4,262,020 | 4/1981 | Ehrenfreund | 564/44 |
| 4,468,405 | 8/1984 | Rigterink et al. | 424/322 |
| 4,798,837 | 1/1989 | Drabek et al. | 514/594 |
| 4,925,875 | 5/1990 | Drabek | 514/594 |
| 4,925,876 | 5/1990 | Drabek | 514/594 |
| 4,973,589 | 11/1990 | Barnett et al. | 514/245 |
| 5,132,325 | 7/1992 | Drabek et al. | 514/594 |
| 5,153,224 | 10/1992 | Drabek et al. | 574/594 |
| 5,288,756 | 2/1994 | Drabek et al. | 514/594 |
| 5,416,102 | 5/1995 | Barnett et al. | 514/351 |
| 5,556,883 | 9/1996 | Thoms et al. | 514/594 |

FOREIGN PATENT DOCUMENTS

| | | |
|---|---|---|
| A-68094/87 | 8/1987 | Australia . |
| 87/71748 | 10/1987 | Australia . |
| 194688 | 9/1986 | European Pat. Off. . |
| 221847 A2 | 5/1987 | European Pat. Off. . |
| 0243790 A2 | 11/1987 | European Pat. Off. . |
| 263438 A2 | 4/1988 | European Pat. Off. . |
| 290392 A1 | 11/1988 | European Pat. Off. . |
| 3827133 A1 | 2/1989 | Germany . |
| 2166134 A | 4/1986 | United Kingdom . |
| WO 94/03066 | 2/1994 | WIPO . |
| WO 95/16354 | 6/1995 | WIPO . |

OTHER PUBLICATIONS

Meazza et al, Pestic. Sci., vol. 35, pp. 137–144, 1992.

Journal of Economic Entomology (Oct., 1996), vol. 89, No. 5, pp. 1156–1160, Nan–Yao Su and Rudolf H. Scheffrahn, "Comparative Effects of Two Chitin Synthesiss Inhibitors, Hexaflumuron and Lufenuron, in a Bait Matrix Against Subterranean Termites (Isoptera:Rhinotermitidae)".

*Primary Examiner*—Shailendra Kumar
*Attorney, Agent, or Firm*—Donald R. Stuart

[57] ABSTRACT

Compounds of formula (I):

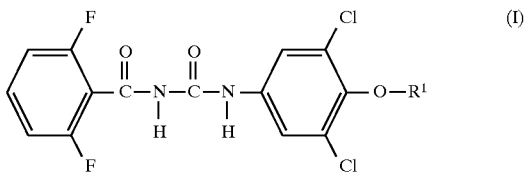

wherein $R^1$ is $-CF=CFCF_3$ or $-CF_2CF=CFCF_3$ are useful in control of cockroaches, ants, fleas, or termites.

8 Claims, No Drawings

BENZOYLPHENYLUREA INSECTICIDES AND METHODS OF USING THEM TO CONTROL COCKROACHES, ANTS, FLEAS, AND TERMITES

CROSS REFERENCE TO RELATED APPLICATION

This patent application claims the benefit of Provisional U.S. Pat. Application Ser. No. 60/029,742 filed Nov. 8, 1996.

BACKGROUND OF THE INVENTION

This invention provides novel benzoylphenylurea insecticides and novel methods of control cockroaches, ants, fleas, and termites.

A broad class of benzoylphenylurea insecticides is disclosed in U.S. Pat. No. 3,748,356. Hexaflumuron, a commercially significant benzoylphenylurea, is disclosed in U.S. Pat. No. 4,468,405. Use of hexaflumuron in methods of controlling termites is disclosed in WO 93/24011. Use of hexaflumuron to control cockroaches is disclosed in WO 94/03066.

We have discovered that certain novel benzoylpheylureas have substantially greater activity against cockroaches, ants, fleas, and termites than would have been expected based on comparison with the closest prior art, i.e., hexaflumuron.

SUMMARY OF THE INVENTION

The invention provides new compounds of formula (I):

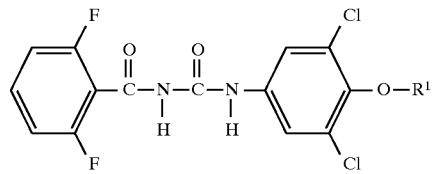

wherein $R^1$ is —CF=CFCF$_3$ or —CF$_2$CF=CFCF$_3$.

The invention also provides a method of controlling cockroaches, ants, fleas, or termites which comprises delivering an effective amount of a compound of the formula (I) to a location where control of cockroaches, ants, fleas, or termites is desired.

DETAILED DESCRIPTION OF THE INVENTION

Intermediate 1: 2,6-difluorobenzoyl isocyanate

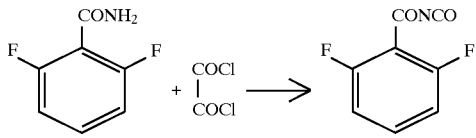

A mixture of 0.52 g of 2,6-difluorobenzamide and 0.33 ml of oxalyl chloride was stirred under reflux in 15 ml 1,2-dichloroethane overnight. Solvent was removed under vacuum and 10 ml 1,2-dichloroethane was added. Solvent was removed under vacuum to leave the title intermediate, which could be used directly or dissolved in 1,2- dichloroethane and stored for future use.

Intermediate 2: 3,5-dichloro-4-(1,2,3,3,3-pentafluoropropenoxy)aniline

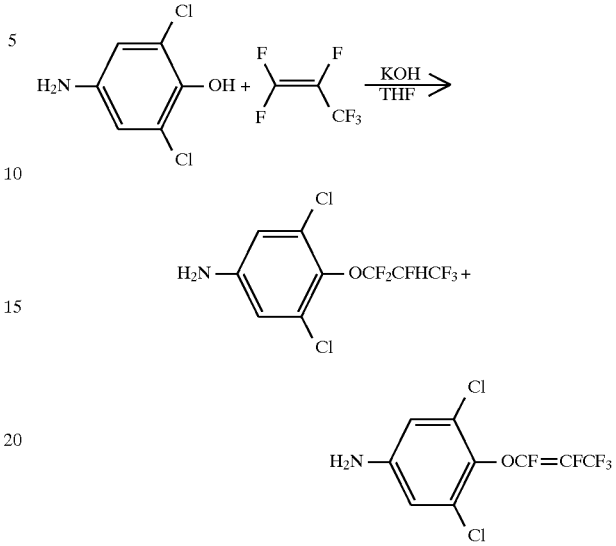

To 1.1 liters of tetrahydrofuran containing 44.5 g of 2,6-dichloro-4-aminophenol and 3.2 g potassium hydroxide, was added subsurface 38.7 g of hexafluoropropene. The addition was complete in 25 minutes at a temperature of 8°–11° C. Analysis by liquid chromatography indicates no starting aniline present. Most of the THF was removed under vacuum, 500 mL water was added and the resulting mixture was extracted 3×500 mL ethyl ether. The combined extracts were washed with 2×100 mL 1N NaOH, 2×200 mL brine, dried over anhydrous sodium sulfate, filtered and the solvent removed under vacuum to give a mixture. This mixture was separated by prep LC to give 46.8 g of 3,5-dichloro-4-(1,1,2,3,3,3-hexafluoropropoxy)aniline and ~4 g of 3,5-dichloro-4-(1,2,3,3,3-pentafluoropropenoxy) aniline. Proton and $^{19}$F nmr and mass spectra were consistent with the proposed structures.

Intermediate 3: 3,5-Dichloro-4-trans-(1,1,2,3,4,4,4-hettafluorobut-2-enoxy)aniline A. Preparation of Sodium Perfluoropentanoate

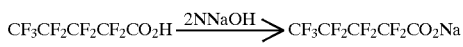

26 g Perfluoropentanoic acid was stirred magnetically as 2N aqueous sodium hydroxide was added dropwise until the pH reached 5. The water was removed under vacuum to yield 28.2 g white solid product, mp 256–7o. The $^{19}$F nmr was consistent with the proposed structure. Anal. Calcd C$_5$F$_9$NaO$_2$: C, 21.0. Found: C, 20.89, H, 0.06, N, 0.02.

B. Preparation of Octafluoro-1-butene

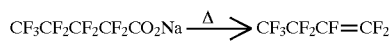

28 g of sodium perfluoropentanoate was placed in a 100 ml round-bottom flask and heated with a mantle with no stirring. The flask was fitted with a tube which went through a trap, a 30% aqueous sodium hydroxide bubbler (containing some Dow Corning Antifoam A to control foaming), and a Drierite tube before the product was allowed to bubble into a reaction mixture. Heating was controlled so as to maintain a steady, but not too vigorous rate of bubbling through the trap.

C. Preparation of 3,5-Dichloro-4-trans-(1,1,2,3,4,4,4-heptafluorobut-2-enoxy)aniline

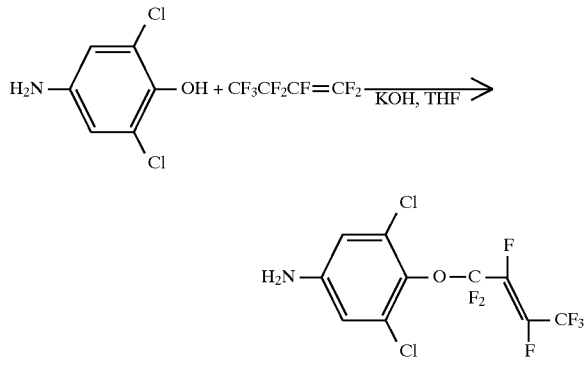

The butene generated in the above reaction was bubbled in subsurface to 14 g 4-amino-3,5-dichlorophenol in 175 ml THF containing 5.15 g 87% powdered potassium hydroxide pellets cooled in an ice bath over 2.5 hours. Stirring was continued while the mixture was allowed to warm to room temperature. The solvent was removed under vacuum and 300 ml dichloromethane was added. This solution was washed with 100 ml water, 100 ml 1N sodium hydroxide, 100 ml 1N HCl, and again with 50 ml 1N NaOH before drying over anhydrous magnesium sulfate. Removed solvent under vacuum to leave a dark oil. This was chromatographed over silica gel starting with 1:1 hexane-dichloromethane and eluting product with dichloromethane. The total yield of nearly colorless oil was 15 g. Anal. calcd $C_{10}H_4Cl_2F_7NO$: C, 33.55; H, 1.13; N, 3.91. Found: C, 33.32; H, 1.12; N, 3.81. Proton and $^{19}F$ nmr confirm the olefinic structure as shown with a trans configuration around the double bond.

PREPERATION OF PRODUCTS

Compound 1: N-[3,5-Dichloro-4-(1,2,3,3,3-pentafluoropropenoxy)phenyl]-N'-(2,6-difluorobenzoyl) urea

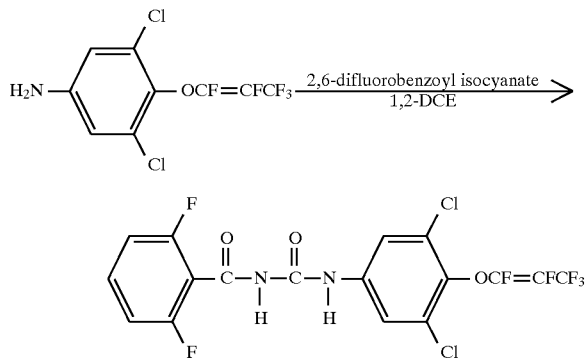

Dissolve 0.77 g 3,5-dichloro-4-(1,2,3,3,3-pentafluoropropenoxy) aniline in 8 mL 1,2-dichloroethane under an atmosphere of nitrogen at room temperature. Add 0.50 g 2,6-difluorobenzoyl isocyanate dissolved in 5.8 mL dichloroethane dropwise over a 10 minute period. Stir and warm to 40° C. for a 2 hour period. Chill in ice water bath and filter the white solid 0.93 g, mp 177°–80° C. Proton nmr and mass spectra were consistent with the proposed structure. Anal. calcd $C_{17}H_7Cl_2F_7N_2O_3$:C, 41.57; H, 1.44; N, 5.70. Found: C, 41.65; H, 1.31; N, 5.59.

Compound 2:1-(2.6-Difluorobenzoyl)-3-[3,5-dichloro-4-trans-(1,1,2,3,4,4,4-heptafluorobut-2-enoxy) phenyl]urea

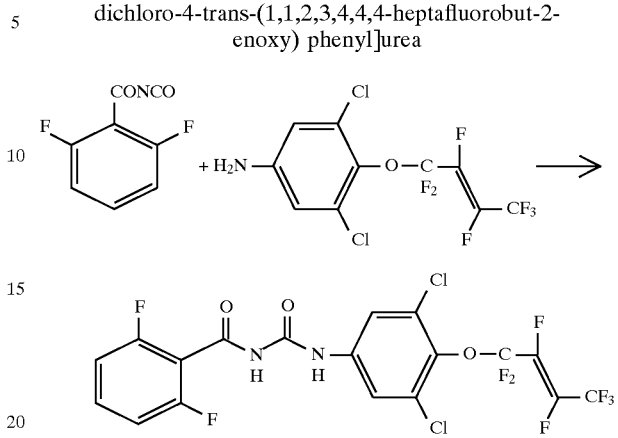

2,6-Difluorobenzoyl isocyanate made from 0.52 g 2,6-difluorobenzamide was stirred in 10 ml 1,2-dichloroethane while 1.08 g of the amine made above in 5 ml 1,2-dichloroethane was added in portions. The mixture was heated to reflux and then cooled. The solvent was removed under vacuum and the resulting solid recrystallized from methanol to give 0.95 g white crystals, mp 153–4o. The proton and $^{19}F$ nmr's were consistent with the proposed structure. Anal. calcd $C_{18}H_7Cl_2F_9N_2O_3$: C, 39.95; H, 1.30; N, 5.18. Found: C, 39.65; H, 1.36; N, 5.19.

BIOLOGICAL ACTIVITY

German Cockroach 2nd Instars (*Blattella Germanica*)

Continuous, low-dose ingestion exposure (treated cornmeal) Rates: (0.19), 0.78, 3.12, 12.5, 50, 200 ppm

|  | $LC_{50}$ (ppm) | |
| --- | --- | --- |
|  | 21 days | 42 days |
| Compound 2 | <1.03 | <0.78 |
| Compound 1 | <0.78 | <0.78 |
| hexaflumuron | >200 | >200 |

Under continuous exposure, Compounds 1 and 2 were far superior to hexaflumuron.

German Cockroach 2nd Instars (*Blattella Germanica*)

Limited ingestion exposure (48 hr) to treated cornmeal Rates: 1, 10, 1,000, 10,000 ppm

|  | $LC_{50}$ (ppm) | | | |
| --- | --- | --- | --- | --- |
|  | 21 days | | 42 days | |
| Compound | low | high | low | high |
| Compound 2 | 60.8 | 1768 | 162.7 |  |
| Compound 1 | 80.2 |  | 36.1 |  |
| hexaflumuron | >10,000 |  | >10,000 |  |

Under limited exposure, Compounds 1 and 2 were far more potent than hexaflumuron.

Cat Flea (*Ctenocephalides felis*)

Continuous exposure of larvae to treated media, impact on subsequent adult emergence Rates: 0.1, 1.0, 10, 100, 1,000 ppm

|  | $LC_{50}$ (ppm) | $LC_{90}$ (ppm) |
| --- | --- | --- |
| Compound 2 | 4.5 | 27.2 |
| Compound 1 | 29.2 | 77.3 |
| hexaflumuron | 65.7 | 333.5 |

Compounds 1 and 2 were far more active against fleas than was hexaflumuron.

Subterranean Termite (*Reticulitermes flavipes*)

Limited exposure (7 days) with mortality determined at 14, 28, 42, and 56 days

| Compound | $LT_{50}$ (days) for 10000 ppm treatment |
| --- | --- |
| Compound 1 | 36.8 |
| Compound 2 | 35.5 |
| hexaflumuron | 40.6 |

Under limited exposure to termites, Compounds 1 and 2 had more rapid action than did hexaflumuron.

Ant Studies

Laboratory ant bait studies were carried out with Red Imported Fire Ant (RIFA) (*Solenopsis invicta*) and Pharaoh Ant (*Monomorium pharaonis*). Chitin synthesis inhibitors, such as the compounds of the invention, control ants by killing the molting larvae and/or pupae and potentially preventing the hatching of eggs. Because adult workers are not affected, control is measured by effects on the brood. The studies involved 3–day exposure to bait. These limited exposure studies more accurately represent real world bait availability than continuous exposure.

| Compound | Concentration tested | Species | Time to Achieve 50% Brood Reduction | Time to Achieve 90% Brood Reduction* |
| --- | --- | --- | --- | --- |
| Compound 1 | 0.07% | RIFA | 2 wks | 3 wks |
|  | 0.07% | Pharaoh | NA | NA |
| Hexaflumuron | 0.1% | RIFA | NA | NA |
|  | 0.25% | RIFA | 4 wks | 10 wks |
|  | 0.1% | Pharaoh | NA | NA |

*Only concentration tested. NA = did not achieve specified percent brood reduction.

Compound 1 is significantly more potent than hexaflumuron based on a short exposure study with RIFA.

FORMULATIONS

In order to facilitate the application of the compounds of formula (I) to the desired locus, or to facilitate storage, transport or handling, the compound is normally formulated with a carrier and/or a surface-active agent.

A carrier in the present context is any material with which the compound of formula (1) (active ingredient) is formulated to facilitate application to the locus, or storage, transport or handling. A carrier may be a solid or a liquid, including a material which is normally gaseous but which has been compressed to form a liquid. Any of the carriers normally used or known to be usable in formulating insecticidal compositions may be used.

Compositions according to the invention contain 0.0001 to 99.9% by weight active ingredient. Preferably, compositions according to the invention contain 0.001 to 10.0% by weight of active ingredient though proportions as low as 0.0001% may be useful in some circumstances.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulfur; natural and synthetic resins, for example coumaronne resins, polyvinyl chloride, and styrene polymers and copolymers; solid polychlorophenols; bitumen; waxes; agar; and solid fertilizers, for example superphosphates. Cellulose based materials, for example wood, sawdust, agar, paper products, cotton linter, or Methocel®, as well as the other solid carriers that are themselves attractive to or at least non-repellant to termites are particularly suitable and preferable. Mixtures of different solids are often suitable. For example, a mixture of wood flour and agar formulated as a moisture containing solid would be preferable.

Suitable liquid carriers include water; alcohols, for example isopropanol and glycols; ketones, for example acetone, methyl ethyl ketone, methyl isobutyl ketone, isophorone and cyclohexanone; ethers; aromatic or aliphatic hydrocarbons, for example benzene, toluene and xylene; petroleum fractions, for example kerosene and light mineral oils; chlorinated hydrocarbons, for example carbon tetrachloride, perchloroethylene and trichloroethane; polar organic liquids, such as dimethyl formamide, dimethyl acetamide, dimethyl sulfoxide and N-methylpyrrolidone; oils derived from plants, such as corn oil and peanut oil. Mixtures of different liquids are often suitable, for example a mixture of isophorone with a polar organic solvent such as N-methylpyrrolidone, as are mixtures of solid and liquid carriers.

Pesticidal compositions are often formulated and transported in a concentrated form which is subsequently diluted by the user before application. The presence of small amounts of a carrier which is a surface-active agent facilitates this process of dilution. Thus it is suitable to use at least one carrier in such a composition which is a surface-active agent. For example, the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sufonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensates of these with ethylene oxide and/or propylene oxide; condensation products of fatty alcohol or alkyl phenols, for example p-octylphenol or p-octylcresol, with ethylene oxide and/or propylene oxide; sulfates or sulfonates of these condensation products; alkali or alkaline earth metal salts, preferably sodium salts, or sulfuric or sulfonic acid esters containing at least 10 carbon atoms in the molecule, for example sodium lauryl sulphate, sodium secondary alkyl sulfates, sodium salts of sulfinated castor oil, and sodium alkylaryl sulfonates such as dodecylbenzene sulfonate; and polymers of ethylene oxide and copolymers of ethylene oxide and propylene oxide.

Pesticidal compositions may for example be formulated as wettable powders, dusts, granules, baits, solutions, emulsifiable concentrates, emulsions, suspension concentrates and aerosols.

Wettable powders usually contain 25, 50 or 75% weight of active ingredient and usually contain in addition to solid inert carrier, 3–10% weight of a dispersing agent and, where necessary, 0–10% weight of stabilizer(s) and/or other additives such as penetrants or stickers.

Dusts are usually formulated as a dust concentrate having a similar composition to that of a wettable powder but without a dispersant, and are diluted in the field with further solid carrier to give a composition usually containing 0.5–10% weight of active ingredient.

Granules are usually prepared to have a size between 10 and 100 BS mesh (1.676–0.152 mm), and may be manufactured by, for example, agglomeration or impregnation techniques. Generally, granules will contain 0.01–75% weight active ingredient and 0–10% weight of additives such as stabilizers, surfactants, slow release modifiers and binding agents. The so-called "dry flowable powders" consist of relatively small granules having a relatively high concentration of active ingredient. Of particular interest in current practice are the water dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulation contain 90% or more by weight of finely divided active material, 3–7% by weight of a blend of surfactants, which act as wetting dispersing, suspending and binding agents, and 1–3% by weight of a finely divided carrier, which acts as a resuspending agent.

Baits are prepared by, for example, combining a mixture of a suitable food source, such as sawdust for termites or grain or meal for cockroaches, with an amount of active ingredient sufficient to provide the desired result; for example, from about 0.001% to about 20% weight active ingredient and forming the mixture into a paste by the addition of about 1% to 5% of a water based binder such as agar. The paste-like mixture may be applied as is or may be packed into a housing such as a hollowed out wooden dowel or a plastic tube or bait station. In other embodiments, sheets of paper or cardboard can be sprayed with or dipped in a diluted formulation containing the active ingredient. Baits are a preferable embodiment of the present invention.

Emulsifiable concentrates usually contain, in addition to a solvent and, when necessary, co-solvent, 10–50% weight per volume active ingredient, 2–20% weight per volume emulsifiers and 0–20% weight per volume of other additives such as stabilizers, penetrants and corrosion inhibitors.

Suspension concentrates are usually compounded so as to obtain a stable, non-sedimenting flowable product and usually contain 10–75% weight active ingredient, 0.5–15% weight of dispersing agents, 0.1–10% weight of suspending agents such as protective colloids and thixotropic agents, 0–10% weight of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions are compositions which may be obtained by diluting a wettable powder or a concentrate with water. The said emulsions may be of the water-in-oil or of the oil-in-water type, and may have a thick 'mayonnaise'-like consistency.

The method of applying a compound of Formula (I) to combat termites comprises applying the compound, conveniently in a composition comprising the compound of Formula (I) and a carrier as described above, to a locus or area to be treated for the termites, such as soil or timber, already subject to infestation or attack by termites or intended to be protected from infestation by termites. The active ingredient is, of course, applied in an amount sufficient to effect the desired action of combatting termite infestation. This dosage is dependent upon many factors, including the carrier employed, the method and conditions of the application, whether the formulation is present at the locus in the form of a film, or as discrete particles or as a bait, the thickness of film or size of particles, the degree of termite infestation, and the like.

Proper consideration and resolution of these factors to provide the necessary dosage of the active ingredient at the locus to be protected are within the skill of those versed in the art. In general, however, the effective dosage of the compound of the invention at the locus to be protected—i.e., the dosage to which the termite has access—is of the order of 0.001 to 1.0% based on the total weight of the composition, though under some circumstances the effective concentration may be as little as 0.0001% or as much as 2%, on the same basis.

When used to control cockroaches, it is preferred to use the active ingredient in a treated bait or as a surface treatment.

When used to control ants, it is preferred to use the active ingredient in a liquid bait or granular bait.

When used to control termites, it is preferred to use the active ingredient in a cellulose based bait.

When used to control fleas, it is preferred to use the active ingredient on a treated substrate.

Suitable formulations include granular, paste, or dust cockroach bait, SP or WP cockroach and/or flea sprayables, cellulose-based termite baits, liquid or granular ant baits, feed-through or topical animal treatment for fleas.

We claim:

1. A compound of formula (I):

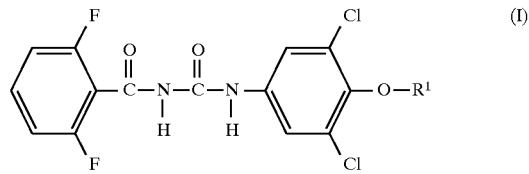

wherein $R^1$ is —CF=CFCF$_3$ or —CF$_2$CF=CFCF$_3$.

2. A compound of claim 1 which is N-[3,5-Dichloro-4-(1,2,3,3,3-pentafluoropropenoxy) phenyl]-N'-(2,6-difluorobenzoyl)urea.

3. A compound of claim 1 which is 1-(2,6-Difluorobenzoyl)-3-[3,5-dichloro-4-trans-(1,1,2,3,4,4,4-heptafluorobut-2-enoxy) phenyl]urea.

4. A method of controlling cockroaches, ants, fleas or termites which comprises delivering an effective amount of a compound of claim 1 to a location where control of cockroaches, ants, fleas or termites is desired.

5. A cockroach bait comprising an effective amount of a compound of claim 1 in combination with a conventional bait matrix.

6. An ant bait comprising an effective amount of a compound of claim 1 in combination with a conventional bait matrix.

7. A composition for contolling fleas comprising an effective amount of a compound of claim 1 in combination with a conventional carrier.

8. A composition for controlling termites which comprises an effective amount of a compound of claim 1 in combination with a conventional carrier.

* * * * *